United States Patent [19]
Kambara et al.

[11] Patent Number: 5,935,794
[45] Date of Patent: *Aug. 10, 1999

[54] METHOD OF DNA BASE SEQUENCE DETERMINATION

[75] Inventors: Hideki Kambara, Hachiouji; Kazunori Okano, Shiki; Hisanori Nasu, Yokohama, all of Japan

[73] Assignee: Hitachi, Ltd., Tokyo, Japan

[ * ] Notice: This patent is subject to a terminal disclaimer.

[21] Appl. No.: 08/969,163

[22] Filed: Nov. 12, 1997

Related U.S. Application Data

[63] Continuation of application No. 08/465,181, Jun. 5, 1995, Pat. No. 5,741,644, which is a continuation of application No. 08/086,892, Jul. 7, 1993, abandoned.

[30] Foreign Application Priority Data

Jul. 7, 1992 [JP] Japan ................................. 4-180095

[51] Int. Cl.[6] .............................. C12Q 1/68; C12P 19/34; C07H 21/02; G01N 33/533
[52] U.S. Cl. .......................... 435/6; 435/91.1; 435/91.2; 435/973; 536/23.1; 536/24.3; 536/24.31; 536/24.32; 536/24.33; 436/527; 436/518; 436/809
[58] Field of Search .............................. 435/6, 91.1, 91.2, 435/973; 536/23.1, 24.3, 24.31, 24.32, 24.33; 436/527, 518, 809

[56] References Cited

U.S. PATENT DOCUMENTS

| | | | |
|---|---|---|---|
| 5,445,934 | 8/1995 | Fodor et al. | 435/6 |
| 5,503,980 | 4/1996 | Cantor | 435/6 |
| 5,741,644 | 4/1998 | Kambara et al. | 435/6 |
| 5,795,714 | 8/1998 | Cantor | 435/6 |

OTHER PUBLICATIONS

Southern et al, "Analyzing and comparing nucleic acid sequences by hybridization to arrays of oligonucleotides: evaluation using experimental models", Genomics 13:1008–1017, Aug. 1992.

Drmanac et al, "Reliable hybridization of oligonucleotides as short as six nucleotides", DNA Cell Biology, 9(7):527–534, 1990.

Khrapko et al, "A method for DNA sequencing by hybridization with oligonucleotide matrix", DNA sequence, 1(6):375–88 Abstract Only, 1991.

Matthews et al, "Analytical strategies for the use of DNA probes", Anal. Biochem. 169:1–25, 1988.

Matera et al, "A transpositionally and transcriptionally competent Alu subfamily", Mol. Cell. Biol. 10(10):5424–5432, Oct. 1990.

*Primary Examiner*—W. Gary Jones
*Assistant Examiner*—Jeffrey Fredman
*Attorney, Agent, or Firm*—Antonelli, Terry, Stout & Kraus, LLP

[57] ABSTRACT

The method of base sequence determination according to the present invention ensures an effective determination of a long DNA base sequence, by providing simultaneous determination of base sequences of two or more positions of the long DNA or base sequences of two or more DNAs, using the DNA probe chip which classifies and retains the DNA oligomers having various sequences, and using fluorophore-labeled primers which have the same sequencies as the oligomers in the chip and are labeled by various fluorophores, then followed by the extension of the determined base length by re-selection of the primers complementary to the sequence thus determined.

10 Claims, 3 Drawing Sheets

METHOD OF DNA BASE SEQUENCE DETERMINATION

This application is a continuation application of Ser. No. 08/465,181, filed Jun. 5, 1995, now U.S. Pat. No. 5,741,644 which application is a continuation application of Ser. No. 08/086,892, filed Jul. 7, 1993 (now abandoned.

BACKGROUND OF THE INVENTION

The present invention relates to the method of DNA or RNA base sequence determination, in particular to the method of base sequence determination for long DNA or RNA having more than 500 base in length.

According to the conventional method, DNA base sequence determination is implemented in the order of DNA fragmented sample preparation process, separation by gel electrophoresis, detection of the separated DNA band pattern, and sequence determination. To describe this method of DNA base sequence determination with reference to the dideoxy chain termination method; the target DNA fragment is inserted into the M13 phage to transform sensitive bacteria, and the transformed bacteria is cultured to increase its copies from which the single strand DNA is prepared. For DNA sequencing, the specific position of the single strand DNA is hybridized with oligonucleotides, then the complementary DNA strand is synthesized through DNA polymerase reaction. The reaction mixture consists of the deoxyribonucleic acid labeled with a radioisotope, in addition to four types of deoxyribonucleic acids serving as substrates. Dideoxyribonucleic acids are further added to it to produce short DNA fragments terminated at special base species. Using the dideoxyribonucleic acids, the operation is performed for obtaining the DNA fragment families having the terminal bases of A, G, C and T, respectively. These DNA fragments are separated by a gel electrophoresis, and then the separated DNA band pattern is detected, thereby determining the DNA base sequence.

According to the said method, DNA fragments have conventionally been detected by the autoradiography in which DNA fragments are labeled by radioisotope. Because of handling inconvenience, however, DNA has come to be labeled by the fluorophore (L. M. Smith et al; Nature, Vol. 321, PP. 674–679(1986) and J. M. Prober et al; Science, Vol. 238, PP. 336–341 (1987)). This method permits analysis of up to about 500 base in length for each DNA. When the base length is greater, the DNA band separation is poorer and signal intensity is substantially reduced, making the analysis very difficult. Longer base areas are analyzed by (1) the method wherein the oligomer complementary to the sequence close to the terminal of the analyzed DNA sequence is prepared and is used as a new primer to determine longer sequences successively (primer walking), and (2) the method wherein one side or both sides of the target DNA are degraded with enzyme, inserted into a vector and then analyzed.

The primer walking technique is effective to ensure reliable determination of the long DNA sequence, but it is accompanied by the problem that a new primer has to be synthesized for every DNA analysis. Instead of synthesizing oligomers each time, it is possible to prepare a set of oligomers which include all different base sequences. At shortest 10 mers are necessary for priming DNA polimerase reaction. Because the shorter oligomers do not produce stable base pairs. A large number of oligomers such as $4^{10} \cong 10^6$ have to be prepared for the set. This is not practical. The number of required oligomers should be reduced to less than 1000. Furthermore, the primer, walking method requires a lot of electrophoresis operations repeatedly, which is also a great trouble. To solve this problem, an attempt is made to form an oligo-nucleotide array which has various kinds of oligomers on a solid surface. DNA to be analyzed is put on the surface to hybridize to the complementary oligomer sites. The hybridized oligomer sequences overlap with one another, by preparing the oligomers having all combinations of 8 to 10 base lengths of different base sequences and by detecting whether or not it is to be hybridized with the target DNA (Z. Strezoska et al; Proc. Natl. Acad. Sci. USA, Vol. 88, PP. 10089–10093 (1991)). This method uses successive hybridization, not primer extending; it does not need electrophoresis. Theoretically one it should be able to determine the sequence of long DNA fragments, but it requires use of a great number of primers with different denaturing temperature, and cannot obtain hybridization conditions to fill all the sequences. It is difficult to determine all sequences according to this method. Furthermore, since determination of the repeated sequences is likely to be indefinite, the target DNA must be made into short fragments in advance, and the long DNA must be analyzed little by little; this requires much trouble.

SUMMARY OF THE INVENTION

The object of the present invention is to solve the above problems and to provide an effective method of DNA base sequence determination by dideoxy chain termination method, which minimized partial determination of sequences, repeated synthesis of new primers based thereon and does not require much time.

To achieve the above object, the present invention uses the reduced DNA oligomer set which includes oligomers having the sequence of a restriction enzyme cutting site or a repetitive sequence in the genome and variety of base sequences on the 3' terminus or 5' terminus. The presence of a known sequence such as cutting site sequences of restriction enzymes in the oligomers reduces the number of oligomers required for the set although the required base length is more than 10 bases from the view point of stability of hybridization. The method of DNA base sequence determination according to the present invention has the steps of:

i) preparing the probe chip where various DNA oligomers which include a base sequence of a restriction enzyme cutting site or a base sequence of repeatedly appeared sequence in genome, and which may become primers are immobilized to respective divided areas, and a set of primers comprising the DNA oligomers labeled by a fluorophore, which have substantially the same sequences as those of said various DNA oligomers, ii) digesting the DNA to be measured at a specific sequence portion employing a restriction enzyme or the like, iii) introducing a fluorophore into the digested portion of the DNA digested in step ii), iv) denaturing the double strand DNA labeled by fluorophore in step iii) to make it into the single strand DNA, or decomposing the terminal with enzyme to make it into the single chain terminal portion, v) hybridizing the single chain DNA made in step iv) with the said DNA oligomers on the probe chip, vi) conducting fluorescence detection of the probe chip cell hybridized the sample and determining the primers which can prime the polymerase reaction, vii) selecting the fluorophore-labeled primers having substantially the same base sequences as those of primers which can be hybridized as determined in step vi) and hybridizing them to the single chain DNA sample made in step iv), viii) making the DNA strand complementary to the DNA sample using the fluorophore-labeled primer, ix) determining the base sequence by electrophoresis of the extension reaction products in step viii), x) hybridizing the fluorophore-labeled primer, which is complementary substantially to the DNA sequence of the determined portion of the base sequence in the preceding steps (complementary position should be as close as possible to the 3' terminal to ensure efficiency), and which is selected from the predetermined primer set, to the said single strand DNA sample, xi) extending the fluorophore-labeled primer hybridized in step x), using the DNA polymerase, xii) determining the base sequence with respect to about 500 base length of the DNA obtained by the extending of the fluorophore-labeled primer in step xi), and, xiii) repeating steps x) to xii) until the complete determination of all the DNA sample base sequences.

The term "substantially" used in the above description should be interpreted to mean that hybridization is possible even if the base sequence is slightly different from the desired one. The restriction enzyme used in step ii), is typically, NotI or SfiI, but any restriction enzyme can be used. The probe chip prepared in step i) is substantially the same as the oligomer chip for determining primers described in the Specifications of the Japanese Patent Application No. 4-042829 (Filing Date of Application: Feb. 28, 1992) and Specifications of the U.S. patent application Ser. No. 08/021, 667 (Filing Date of Application: Feb. 24, 1993), except that the accessories such as an electrode are not necessary, only the primers are immobilized and that the cell pattern may be different from that of the oligomer chip. Furthermore, gel electrophoresis can be employed for determination of the base sequence in steps ix) and xii).

As described above, in order to avoid partial sequence determination and repeated synthesis of new primers based thereof in the method of DNA base sequence determination by the dideoxy chain termination method of the conventional technology, the method of DNA base sequence determination according to the present invention prepares a set of candidates for primers in advance and selects the primers which are complementary to the target DNA.

The present invention provides simultaneous determination of base sequences of two or more positions of the long DNA or two or more DNAS, using the "DNA probe chip which classifies and retains the DNA oligomers having various sequences" and "fluorophore-labeled oligomers where each of the sets of these oligomers are labeled by various fluorophores" (steps i) to ix)). This is followed by primer extending, using the specified fluorophore-labeled oligomer set (above steps x) to xiii)), thereby saving a great deal of time.

For the oligomer set which is to become primers, it is possible to label the primers with the same fluorophore. When the DNA is sequenced simultaneously from plural portion where the primers are hybridized, the number of types of the primers must be six or less, and each primer must be labeled by a different fluorophore; when each of the DNAs hybridized by two or more types of primers is divided into plural portions and is sequenced in a different reaction vessel using one primer each, each primer may be labeled by the same fluorophore.

Essentially, the present invention relates to the nucleic acid base sequence determination using the primer set comprising the oligonucleotides including the sequence complementary to recurrent sequences in the genome, and containing the oligonucleotides having variety of sequences (e.g. such portion as NNN of sequence in Table 1) different from the said complementary sequence on the 3' or 5' terminal side in the nucleic acid base sequence determination.

The sequence recurrent in the said genome includes the sequence at the digested portion of the restriction enzyme or Alu sequence.

Furthermore, the present invention provides a method of nucleic acid base sequence determination where at least part of the said primer set comprises the oligonucleotide containing the sequence complementary to the promoter sequence recognized by the RNA polymerase; it also provides a method of nucleic acid base sequence determination characterized in that at least part of the said primer set is the oligonucleotide of the sequence which bonds complementarily with the oligonucleotide having the ATG or CAT sequence.

Still further, the present invention provides a method of said nucleic acid base sequence determination characterized in that the said primer is labeled by the fluorophore. The fluorophore labeling the primer is used to provide fluorescence detection of the DNA fragment having migrated and reached the predetermined position in gel electrophoresis.

The following substances can be used as a fluorophore for the present purpose; rhodamine type fluorophore such as sulforhodamine 101, phycobilliprotein such as B-phycoerythrin and R-phycoerythrin, fluorescein, 4-nitrobenzo-2-oxa-1, 3-diazol, phthalocyanine, Nile blue and their derivatives, as well as polymers containing these fluorophores. It should be noted, however, that when phycobilliprotein is used, it is necessary to label it by using the biotin-avidin or hapten-antihapten antibody for the probe associated with the target polynucleotide, in order to ensure thermal stability and stability against a denaturant.

The denaturant is, for example, the formamide which denatures the DNA during electrophoresis, and phycobilliprotein has poor resistance against it.

Furthermore, the present invention provides a method of nucleic acid base sequence determination by using the primers which are selected by the use of olygonucleotide probes immobilized on a chip in which each oligonucleotide has the same sequence as that of the primer set.

In the case that DNA is sequenced from plural positions in the DNA strand simultaneously, it is necessary to use plural primers labeled with different fluorophores to distinguish each sequence. Consequently it is necessary to look for the primers which are complementary to a part of the long DNA and are labeled by different fluorophores. For selecting the primers, the DNA is hybridized on the DNA oligomer chip to determine the adequate primers by checking which DNA oligomers they hybridize with. There are various kinds of DNA oligomers, having the same base sequences as those in oligomer set, on the chip. They are classified and arrayed on the chip. When the long DNA has the complementary sequence to one of the oligomers, it is immobilized at the spot on the chip. The DNA captured on the DNA probe chip is detected (fluorescence detection is possible if the DNA to be measured is labeled by a fluorophore in advance), thereby specifying two or more oligomers having the sequence complementary to that in the DNA to be measured. Then the primers having the same sequence as these oligomers hybridized with the DNA and labeled by the different fluorophore are selected to be the first primers. Starting with these primers, the base sequences are determined simultaneously from two or more positions (said steps vii)–ix)). Then the second primers, which is used to determine the next base sequence, are selected in a way that their base sequences are complementary to the determined base sequences in the determined 3' terminal region. Repetition of this operation provides highly efficient determination of the long DNA base sequence.

The above has described the case where two or more oligomers are specified and two or more primers are used to determine base sequences simultaneously at the same number of positions as those of the primers. It is also possible to determine the base sequence at one position using one primer.

As the oligomer set in this case, it is convenient to use the oligomers which contain the repetitive known sequences, appearing in the digested portion of the restriction enzyme or in human genome and di-to hexamer having various sequences at the terminal for identifying the DNA to be measured. Although the di-to hexamer parts alone in the oligomers do not give sufficient hybridization force, the known parts together with the di-to hexamer parts give large hybridization force. Therefore, the use of the coupled oligomers is very convenient to realize stable hybridization as well as to reduce the number of oligomers required for the selection.

Effective sequence determination of a RNA transcription portion in the target DNA is made possible by using the set which contains various oligonucleotide sequences complementarily bonded to the promoter area recognized by RNA polymerase, for example, to the TATA box or CAAT box. The probability of recognizing the open reading frame of the gene will be increased by using an oligonucleotide set having the sequence ATG as a starting point for peptide synthesis or the sequence CAT complementary thereto as a part. This is convenient to determine the sequence of the protein code area.

The above has described the DNA base sequence determination. RNA base sequence determination is made possible by converting the target RNA into the DNA by the reverse transcriptase or the like, and by determining the base sequence of that DNA according to the above procedure.

DESCRIPTION OF PREFERRED EMBODIMENTS

The present invention will be described with reference to the embodiments. Table 1 illustrates the base sequence of five examples of primers used in the following embodiments:

TABLE 1

| | |
|---|---|
| Sequence number | 1 |
| Sequence length | 9 |
| Sequence type | nucleic acid |
| Number of chains | 1 |
| Topology | straight chain |
| Type of sequence | Synthetic DNA primer |
| Sequence characteristics | N in the sequence can be any ACGT. |
| Sequence | GAATTCNNN |
| Sequence number | 2 |
| Sequence length | 10 |
| Sequence type | nucleic acid |
| Number of chains | 1 |
| Topology | straight chain |
| Type of sequence | Synthetic DNA primer |
| Sequence characteristics | N in the sequence can be any ACGT. |
| Sequence | GAATTCNNNN SEQ ID NO:1 |
| Sequence number | 3 |
| Sequence length | 8 |
| Sequence type | nucleic acid |
| Number of chains | 1 |
| Topology | straight chain |
| Type of sequence | Synthetic DNA primer |
| Sequence characteristics | N in the sequence can be any ACGT. |
| Sequence | AGCTNNNN |
| Sequence number | 4 |
| Sequence length | 12 |
| Sequence type | nucleic acid |
| Number of chains | 1 |
| Topology | straight chain |
| Type of sequence | Synthetic DNA primer including other sequences |
| Sequence characteristics | O, P and Q in the sequence are TTX, TCX, TAX, TGX, CTX, CCX, CAX, CGX, ATX, ACX, AAX, AGX, GUX, GCX, GAX, and GGX (where X is a spacer). |
| Sequence | ATGOPQ |
| Sequence number | 5 |
| Sequence length | 8 |
| Sequence type | nucleic acid |
| Number of chains | 1 |
| Topology | straight chain |
| Type of sequence | Synthetic DNA primer |
| Sequence characteristics | N in the sequence can be any ACGT. |
| Sequence | TATANANN |

EMBODIMENT 1

Figure 1:
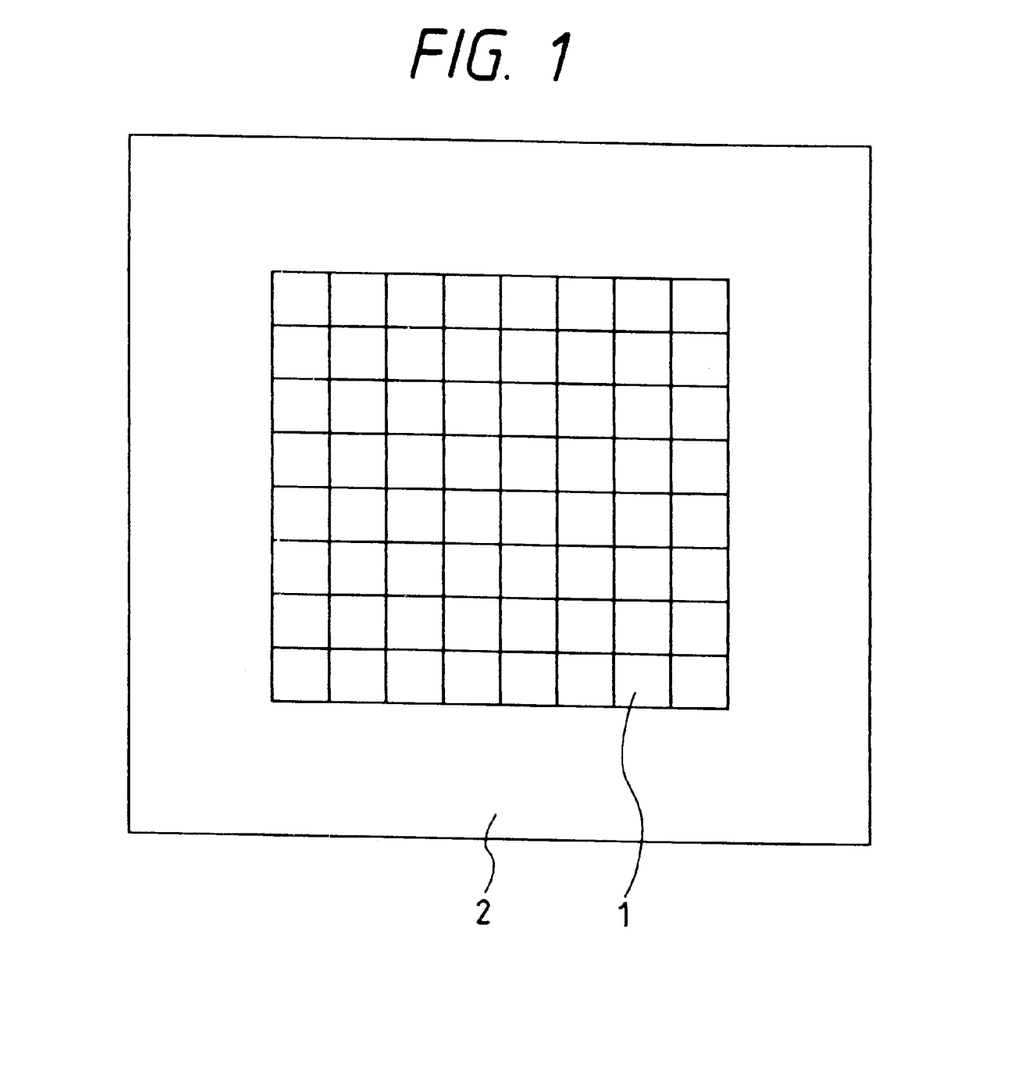
FIG. 1 is a schematic plan view representing the DNA probe chip.
Figure 2:
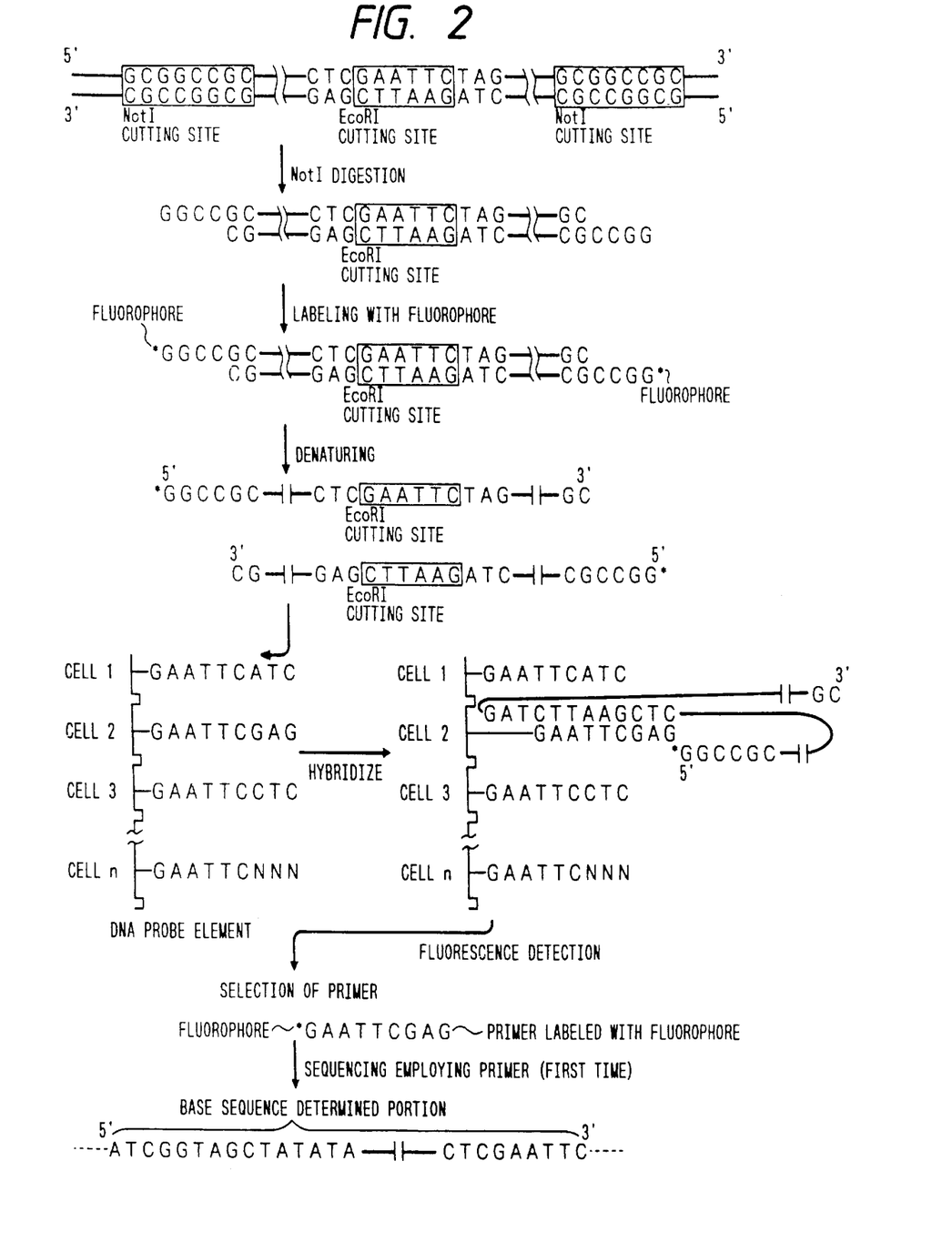
FIG. 2 is a schematic view representing the flow of the steps up to the first base sequence determination in an embodiment of the present invention with the DNA sequences being SEQ ID NO: 2, SEQ ID NO: 3 and SEQ ID NO: 4.

The present embodiment will be described with reference to FIGS. 1 and 3. This embodiment shows the case of base sequencing using the base sequence of the portion of the DNA which can be digested by the restriction enzyme EcoRI. As illustrated in FIG. 2, EcoRI recognizes the sequence GAATTC and digests between G and A. So the complementary chain 5'GAATTCNNN3' (N can be any desired nuclear acid) described in sequence number 1 of Table 1 is created and is immobilized to each cell on the chip surface, to be used as a probe. As they are four base species (A, C, G and T), the number of possible configuration of NNN is 64 (43). All of 64 oligomers are produced and immobilized on the DNA probe chip in the matrix as shown in FIG. 1. Here the oligomers can have the extra nucleotides besides the cutting cite sequence and NNN.

DNA probe chip in FIG. 1 comprises (1) reaction cells 1 on which each of 64 oligomers (probes) are immobilized, and (2) another area 2 which is used as a reference position to measure the non-specific adsorption amount (corresponding to the fluorescence intensity like background) of the labeled probe and which is also used for manipulation of the chip.

Each of the cells in the matrix of the reaction portion of the DNA probe chip measures 1 mm by 1 mm, and the reaction portion where 64 of these cells are arranged measures 8 mm by 8 mm. The method of producing the DNA probe chip is described in the last part of the description of the present embodiment. In addition to this chip, a set comprising 512 fluorophore-labeled primers of 8- or 10-base length of the sequence numbers 2 and 3 on Table 1 is prepared. The primer set comprising 512 oligomers from the sequence numbers 2 and 3 on the table 1 has been used in the present embodiment. Generally, 200 to 1,000 types (or still more) of oligomers are enough for the set. Primers are labeled by various fluorophores whenever required. They also include primers including cutting site sequences of various restriction enzymes and primers containing the terminal of repetitive sequences.

The target DNA is digested by the restriction enzyme NotI and the fluorophore is introduced into the digested portion. The fluorophore can be introduced by various ways; for example, the fluorophore-labeled nucleotide monomer is introduced by polymerase reactions, the fluorophore-labeled oligonucleotide is bonded by ligation reactions, biotin is introduced into all the DNA chains and the fluorophore-labeled avidin or the like is bonded to biotin, or DNA is converted to have fluorescence by etheno-reaction. All of these methods are widely known. Here, fluorophore-labeled oligomer by ligation will be introduced as an example in the following description:

The advantage of employing the ligation reaction, by which fluorescent labeled oligomers (usually from 10 mer to 20 mer) are connected with the digested terminus, is that the length of terminus sequence can be very long including the cutting site sequence. This is good for getting stable hybridization using long oligomers (primers). The hybridization stability and the selectivity of primers can be controlled independently by putting dimer to hexamer following the known sequence part of the oligomers. This is especially useful in the case of using four base cutter enzymes because the cutting site sequence is very short and it is difficult to obtain stable hybridization force if the oligomers consist only from the cutting site sequence followed by short oligonucleotide such as hexamer.

NotI is a restriction enzyme which recognizes the base sequence GCGGCCGC and digests the portion between the GC and GG. Fluorophore labeled oligomers are introduced into the digested terminus.

After the fluorophore-labeled DNA are denatured by alkali denaturation to be single stranded DNA, they are hybridized with probes on the chip and washed. Then the hybridized cells on the chip by the sample are recognized by a fluorescent measurement. The outline of the reaction and related items used in this case is the same as the description of said Z. Strezoska et al, Proc. Natl. Acad. Sci. USA, Vol. 88, PP. 10089–10093 (1991)). Sequencing reactions (e.g. said steps vii) ad viii)) are carried out, using the fluorophore-labeled primer containing the same sequence as those of the DNA probes of the hybridized portions. In the present embodiment, sequence determination is carried out up to 500 bases from two positions of the target DNA in one lot, using the two types of primers labeled by the different fluorophores.

Figure 3:
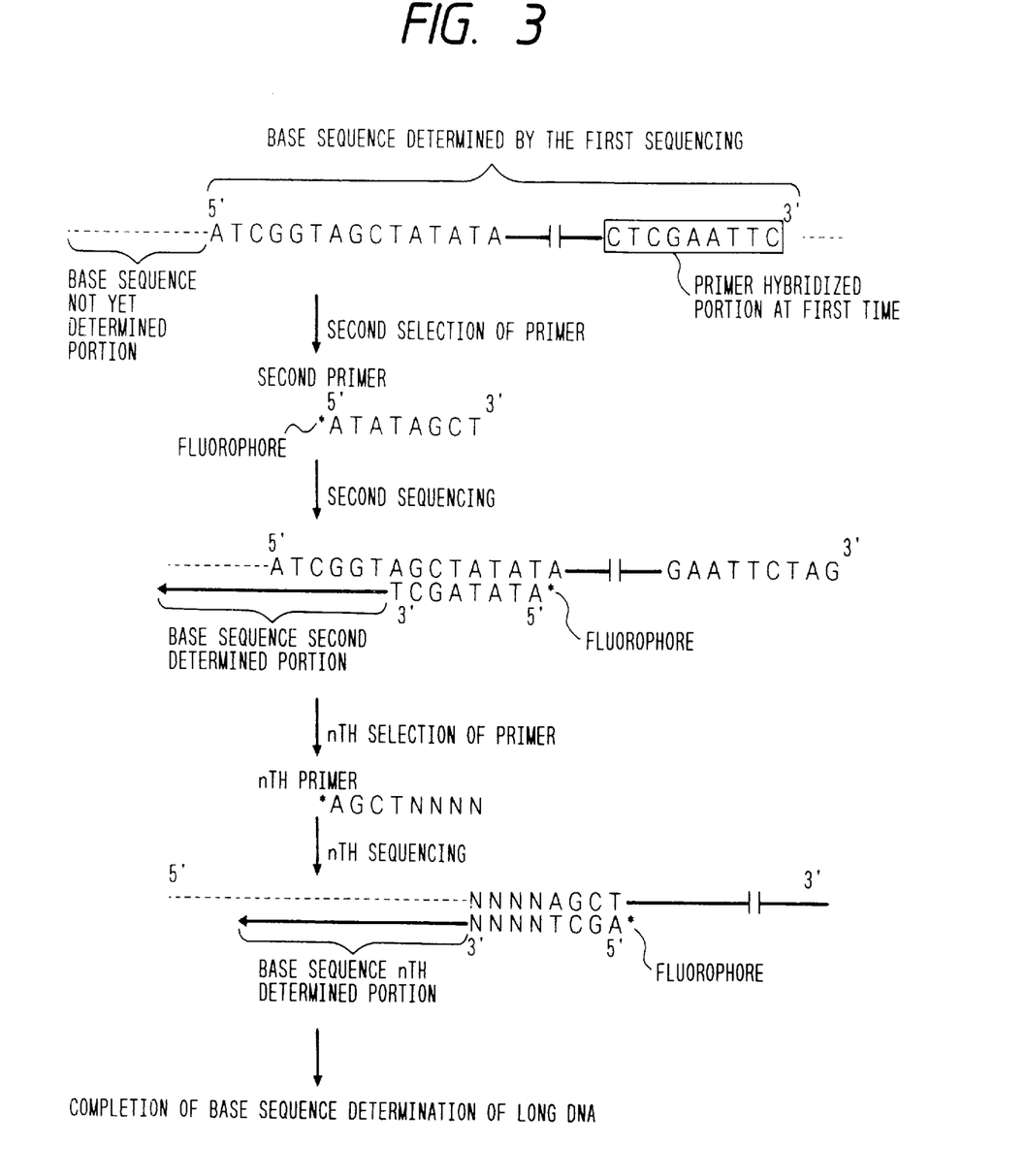
FIG. 3 is a schematic view representing the flow of the steps on and after the second base sequence determination in an embodiment of the present invention with the DNA sequences being SEQ ID NO: 1 and SEQ ID NO: 4.

As shown in FIG. 3, the sequences in the range of 400- to 500-base in length of the already determined DNA sequences which are matched with some of primers currently available in the set of the 512 types of primers are selected as the second primer sequence and the second sequencing is performed, using these fluorophore-labeled primers. The 10 base length primers did not always contain the primers which are completely matched to the 10 bases, but the primers can often be used if the 8 bases at the 3' terminal are matched with each other. Here it is possible to improve the overall seqeuncing efficiency by preparing fluorophore-labeled primers having different fluorescent emission wavelength and simultaneous sequencing of them at several positions.

Likewise, the base sequence determination is conducted on and after the third sequencing; thus a long DNA sequence is determined.

In this way, the present invention provides a method of ensuring an effective DNA sequencing by selecting plural primers, which are complementary to the long DNA, from a set of primers prepared in advance.

The following describes how to prepare the DNA probe chip used in the above embodiment: Firstly, the surface of the glass or silicon wafer is subjected to vapor oxidation. Here vapor oxidation is essential for the surface amino-silanization in the next process, but it is not necessary to form the thick oxidized layer as in the case of forming the insulation film in the ordinary semi-conductor manufacturing process. Next, using the 3-(2-aminoethylaminopropyl) trimethoxysilane, the surface of the oxidized film is subjected to amino-silanization to introduce the amino residue onto the wafer surface. The amino residue is protected with trifluoroacetic acid. Then apply the positive type resist composed of phenolnovolak resin system provided with quinonediazide, and bake it at the temperature of 95° C. This resist permits removal of the exposed portion by washing with alkaline solution; so it allows successive immobilization of the different probes at different positions on the wafer by repeating the exposure, washing with alkaline solution, removal of trifluoroacetylated residue and polynucleotide probe immobilization process. Firstly, the first cell on the silicon wafer surface is exposed to the 350 nm to 400 nm light to remove the first cell resist. Then, by washing with the aqueous trimethylammonium solution, the decomposed resist is removed. Likewise, trifluoroacetylated residue protecting the amino residue is removed at the same time. Then according to the method described in "Søren Richard Rasmussen et al; Analytical Biochemistry, Vol. 198, PP. 138 to 142 (1991)", the first probe having phosphate group at the 5' terminal is immobilized. That is, the first probe is made to react at the temperature of 50° C. for five hours in the presence of the pH7 1-metylimidazole buffer solution and 0.2M of 1-ethyl-3-(3-dimethylaminopropyl)-carbodiimide. Likewise, the same process is repeated in the second cell and thereafter, to immobilize the 2nd to 64th probes. Finally all the cells are washed with the aqueous trimethylammonium solution to remove the byproduct of the carbodiimide. The above processes provide the reaction chip having a plurality of independent cells with different probes immobilized on the surface.

EMBODIMENT 2

The present embodiment shows an example of using the oligonucletide of the sequence complementary to the oligonucleotide containing the sequence of ATG or CAT which corresponds to the initiation codon or its anti-codon for the open reading frame of polypeptide.

The polynucleotide used in the present embodiment includes the 12 base length oligonucleotide described in the sequence number 4 of Table 1 wherein the 5' terminal is ATG, and others comprise random combinations of TTX, TCX, TAX, TGX, CTX, CCX, CAX, CGX, ATX, ACX, AAX, AGX, GUX, GCX, GAX and GGX consisting of three bases each; the amino residue bonded to the 5' terminal through the spacer. Thus, 4096 types of polynucleotide probes are used in the present embodiment. Here X is a spacer, and is composed of the substances which do not specifically bond with each base. Each probe is immobilized to each cell of the reaction chip according to the technique of Embodiment 1. Each cell in the matrix of the reaction port of the DNA probe chip measures 0.5 mm by 0.5 mm, while the reaction portion measures 32 mm by 32 mm. The target DNA is digested by the NotI as in the case of Embodiment 1, and the fluorophore is introduced into the digested portion. The present embodiment uses the following procedure for fluorophore labeling: According to the method described in "Larry E. Morrison et al; Analytical Biochemistry 1.83, 231–244 (1989)", the phosphate group is introduced into the 5' terminal of said sample polynucleotide, using the T4 polymerase kinase.

It is then made to react for eighteen hours in the pH 6 solution containing the 0.2 M of 1-ethyl-3 (dimethylaminopropyl) carbodiimide and 0.5 M of ethylenediamine, to introduce the amino residue into the 5' terminal. Ethanol precipitation is repeated to remove the ethylenediamine which has not yet reacted; then the reaction product is put into in 0.1M of pH 9 carbonic acid buffer solution including 20% acetonitrile to react with sulforhodamine 101 acid chloride (60 to 100 times higher molar concentration than that of target oligonucleotide) having a final concentration of 20 mM. After removing sulforhodamine 101 residue by ethanol precipitation, we obtain the polynucleotide sample where the 5' terminal is labeled with sulforhodamine 101.

The labeled polynucleotide sample is put on the said probe chip where the 4096 types of probes are immobilized on each cell to hybridize with the probes according to the procedure used in embodiment 1. After the hybridization reaction has completed, the fluorophore labeled DNA are held on some restricted cells on the chip. The held portions are distinguished from the none fluorophore held portions by using the He/Ne laser (594 nm) ( or Na lamp, etc.) and photomultiplier (or highly sensitive line sensor or area sensor), and the cells which keep the labeled DNA are recognized according to the measured intensity of the fluorescence. Needless to say, other light sources or fluorophores can be used in combination.

As in the case of Embodiment 1, sequencing reactions are carried out using the fluorophore-labeled primers having the same sequences as those of the DNA probes of the hybridized portions. In the present Embodiment, the sequencing of target DNA was carried out from two positions and up to 500 bases, using two types of primers labeled by different fluorophores.

As shown in FIG. 3, the primers having sequences, which appear in the range of 400–500 base length of the determined DNA, are selected from 512 types of primers currently available, and the second sequencing is performed, using the same procedure as that in the Embodiment 1.

As described above, the different polynucleotide samples hybridize with the different cells on the chip, according to the present invention. The probes immobilized on the chip used in the present embodiment cover all the possible sequences of 12-mers starting with ATG, so it has an advantage of being used for searching the primers usable for the DNA whose the sequence is unknown. Furthermore, the area of the target polynucleotide starting with ATG may be the initiation cordon of the open reading frame in the DNA, so it is possible to increase the probability of sequencing the area which encodes the polypeptide in the DNA, even if random sequence determination is made.

EMBODIMENT 3

The primer set used in the present Embodiment comprises oligonucleotides which can hybridize with the complementary strand of the promoter area recognized by RNA polymerase, and their sequence is TATANANN as shown by sequence number 5 on Table 1. Since the three of N can take any nucleic acid, the number of possible oligonucleotide species is 64. As in the case of Embodiment 1, they are immobilized in cells on the DNA probe chip surface made of a silicon wafer or glass (in some case, it is plastic). The same oligomers are also used as primers by introducing the fluorophore labeling into the 5' terminal.

The sample DNA is digested with NotI as in the case of Embodiment 1, and the fluorophore is introduced into the cutting sites. In the present Embodiment, the sulforhodamine 101 acid chloride is used as a labeling fluorophore according to the following procedure:

The digested and labeled DNA fragments react with said probe chip, where said probes in 64 combinations are immobilized on the respective cells, under the hybridization conditions according to the Embodiment 1. Said labeled DNA fragments subjected to non-specific adsorption are removed by washing the chip surface.

The fluorescence emitted from the cells in the chip keeping labeled DNA fragments is measured and the cells hybridized with the labeled DNA are recognized by measuring the intensity of the fluorescence.

As in the case of Embodiment 1, sequencing reactions are carried out using the fluorophore-labeled primers having the same sequences as those of the DNA probes of the hybridized portion. In the present Embodiment, the target DNA sequences are determined from the two positions and the determined base lengths are over 500 bases, using two types of primers labeled by different fluorophores.

The primers, having sequences appear in the range of 400- to 500 base length of the determined DNA, are selected from 512 oligomers currently available, and the second sequencing and thereafter is performed, using the same procedure as that in the Embodiment 1.

As described above, the different polynucleotide samples hybridize to the different cells on the chip, according to the present invention. The probes immobilized on the chip used in the present embodiment cover almost half of the oligomer species including the promoter sequences which are normally called the TATA box or Hogness box, so it has an advantage of raising the probability in sequencing the promoter areas of unknown DNA and their transcription area located downstream of them, namely, the RNA. The present Embodiment uses, the oligomers which recognize the sequence complementary to the TATA box. Needless to say, effective results can also be obtained by using the oligomer set which recognizes the complementary sequence in other promoter areas.

EMBODIMENT 4

As in the case of said Embodiments, the DNA probes having the Alu sequence described in sequence number 3 of Table 1 are immobilized on the probe chip, and the target DNA is digested with an enzyme as in the case of Embodiment 1. Then the digested DNA fragments being labeled with fluorophore react with the probes under the hybridization conditions. The primers corresponding to the probes hybridized with the sample DNA are selected from among the primers in the set, and DNA sequence can be determined, according to the same procedure as that in the case of said Embodiments.

As described above, for sequencing the long DNA, the fluorophore-labeled primer set is used to carry out the sequencing from plural positions simultaneously. The sequences which are matched to that of the specified primers are selected from the determined base sequence. More effective long DNA base sequence determination can be ensured by extending the next base length using these primers.

The method according to the present invention eliminates the need of synthesizing every required primer as in the conventional method, thereby ensuring a quick sequencing. The method according to the present invention also permits determination of the sequence from the portion digested by the enzyme and determination of the base sequence hybridized to the sequences recurring in the human gene, without taking the trouble of cloning, etc.

Furthermore, for the unknown DNA sample, this method raises the probability of analyzing preferentially the RNA transcription portion and polypeptide coding area, by applying the set which recognizes the seqeunce of RNA transcription promoter portion or polypeptide translation initiating portion.

---

What is claimed is:

1. A DNA probe chip comprising:

a solid substrate having a predetermined number of cells, and a set of DNA oligomers having a predetermined number of DNA oligomers immobilized on the substrate, wherein each DNA oligomer has a first sequence part and a second sequence part connecting directly to the first sequence part, wherein each of the DNA oligomers has the first sequence part having an identical sequence in all of the DNA oligomers, and wherein the second sequence part of each DNA oligomer of the set of DNA oligomers has a sequence which is different from each other second sequence part in the set of DNA oligomers, and one terminal portion of the first sequence part is immobilized on the cell, and wherein the length of the first sequence part is equal to or longer than 4 mers, the length of the second sequence part is 2 mers to 6 mers, and the length of each of the DNA oligomers is equal to or longer than 10 mers.

2. The DNA chip according to claim 1, wherein the predetermined number of the DNA oligomers is equal to or less than 4096.

3. DNA probe chip according to claim 1, wherein the first sequence part is an Alu sequence, which is also a repetitive element in a genome.

4. A DNA probe chip comprising:

a solid substrate having a predetermined number of cells, and a set of DNA oligomers having a predetermined number of DNA oligomers immobilized on the substrate, wherein each DNA oligomer has a first sequence part having an identical sequence in all of the DNA oligomers and a second sequence part connecting directly to the first sequence part and said second sequence part in the set of DNA oligomers has a sequence selected from sequences which constitute all possible sequences for a given number of bases selected from the group consisting of A, T, G, and C; and wherein one terminal portion of the first sequence part is immobilized on the cell, and the length of the first sequence part is equal to or longer than 4 mers, the length of the second sequence part is 2 mers to 6 mers, and the length of each of the DNA oligomers is equal to or longer than 10 mers.

5. A DNA probe chip comprising:

a solid substrate having a predetermined number of cells, and a set of DNA oligomers having a predetermined number of DNA oligomers each of which has a known sequence and is immobilized on a different cell on the solid substrate, wherein each of the DNA oligomers has a first sequence part having an identical sequence in all of the DNA oligomers and a second sequence part connecting directly to the first sequence part and having a sequence selected from sequences which constitute all possible sequences of a plurality of bases selected from the group consisting of A, T, G, and C; wherein one terminal portion of the first sequence part is immobilized on the cell, and the length of the first sequence part is equal to or longer than 4 mers, the length of the second sequence part is 2 mers to 6 mers, and the length of each of the DNA oligomers is equal to or longer than 10 mers.

6. DNA probe chip of according to claim 5, wherein the predetermined number of the DNA oligomers is equal to or less than 4096.

7. A reagent set for base sequence determination comprising:

a set of DNA oligomers having a predetermined number of DNA oligomers each of which has a known sequence, wherein each of the DNA oligomers has a first sequence part having an identical sequence in all of the DNA oligomers and a second sequence part connecting directly to the first sequence part and having a sequence selected from sequences which constitute all possible sequences of a plurality of bases selected from the group consisting of A, T, G, and C; and wherein the length of the first sequence part is equal to or longer than 4 mers, the length of the second sequence part is 2 mers to 6 mers, and the length of each of the DNA oligomers is equal to or longer than 10 mers, and a set of fluorophore-labeled primers, each of which has an identical sequence to that of each of said DNA oligomers.

8. A reagent set for base sequence determination comprising:

a set of DNA oligomers having a predetermined number of DNA oligomers each of which has a known sequence, wherein each DNA oligomer has a first sequence part and a second sequence part connecting directly to the first sequence part, wherein each of the DNA oligomers has the first sequence part having an identical sequence in all of the DNA oligomers, the second sequence part of each DNA oligomer of the set of DNA oligomers has a sequence which is different from each other second sequence part in the set of DNA oligomers, and wherein the length of the first sequence part is equal to or longer than 4 mers, the length of the second sequence part is 2 mers to 6 mers, and the length of each of the DNA oligomers is equal to or longer than 10 mers, and a set of fluorophore-labeled primers, each of which has an identical sequence to that of each of said DNA oligomers.

9. A reagent set for base sequence determination comprising:

a set of DNA oligomers having a predetermined number of DNA oligomers each of which has a known sequence, wherein each DNA oligomer has a first sequence part and a second sequence part connecting directly to the first sequence part, wherein each of the DNA oligomers has the first sequence part having an identical sequence in all of the DNA oligomers, the second sequence part of each DNA oligomer of the set of DNA oligomers has a sequence which is different from each other second sequence part in the set of DNA oligomers, and wherein the length of the first sequence part is equal to or longer than 4 mers, the length of the second sequence part is 2 mers, and the length of each of the DNA oligomers is equal to or longer than 10 mers, and a set of fluorophore-labeled primers, each of which has an identical sequence to that of each of said DNA oligomers.

10. A DNA probe chip comprising:

a solid substrate having a predetermined number of cells, and a set of DNA oligomers having a predetermined number of DNA oligomers immobilized on the substrate, wherein each DNA oligomer has a first sequence part and a second sequence part connecting directly to the first sequence part, wherein each of the DNA oligomers has the first sequence part having an identical sequence in all of the DNA oligomers, and wherein the second sequence part has a sequence selected from sequences which constitute all possible sequences, and one terminal portion of the first sequence part is immobilized on the cell, wherein the length of the first sequence part is equal to or longer than 4 mers, the length of the second sequence part is 2 mers to 6 mers, and the length of each of the DNA oligomers is equal to or longer than 10 mers, and wherein the first sequence part is an Alu sequence, which is also a repetitive element in a genome.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 10 base pairs
        (B) TYPE: nucleic acid
        (C) STRANDEDNESS: single
        (D) TOPOLOGY: linear     (ii) MOLECULE TYPE: DNA    (iii) HYPOTHETICAL: YES     (iv) ANTI-SENSE: NO      (xi) SEQUENCE DESCRIPTION: SEQ ID NO:1:

GAATTCNNNN     10

(2) INFORMATION FOR SEQ ID NO:2:

(i) SEQUENCE CHARACTERISTICS:
        (A) LENGTH: 12 base pairs
        (B) TYPE: nucleic acid
        (C) STRANDEDNESS: single
        (D) TOPOLOGY: linear     (ii) MOLECULE TYPE: DNA    (iii) HYPOTHETICAL: YES     (iv) ANTI-SENSE: NO      (xi) SEQUENCE DESCRIPTION: SEQ ID NO:2:

CTCGAATTCT AG    12

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear     (ii) MOLECULE TYPE: DNA -continued (iii) HYPOTHETICAL: YES (iv) ANTI-SENSE: NO (xi) SEQUENCE DESCRIPTION: SEQ ID NO:3:

GAGCTTAAGA TC            12

(2) INFORMATION FOR SEQ ID NO:4:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (iii) HYPOTHETICAL: YES (iv) ANTI-SENSE: NO (xi) SEQUENCE DESCRIPTION: SEQ ID NO:4:

ATCGGTAGCT ATATA            15